United States Patent [19]

Sackler

[11] Patent Number: 5,733,571
[45] Date of Patent: Mar. 31, 1998

[54] TRANSDERMAL PATCH FOR COMPARATIVE EVALUATIONS

[75] Inventor: David Sackler, Greenwich, Conn.

[73] Assignee: Euro-Celtique, S.A., Luxembourg, Luxembourg

[21] Appl. No.: 583,234

[22] Filed: Jan. 5, 1996

Related U.S. Application Data

[60] Provisional application No. 60/008,391 Dec. 8, 1995.
[51] Int. Cl.$^6$ ............................................. A61F 13/00
[52] U.S. Cl. ............................ 424/449; 424/448
[58] Field of Search ................................ 424/448, 449

[56] References Cited

U.S. PATENT DOCUMENTS

| | | | |
|---|---|---|---|
| 4,379,454 | 4/1983 | Campbell et al. | 604/897 |
| 4,806,341 | 2/1989 | Chien et al. | 424/448 |
| 4,846,826 | 7/1989 | Shaw | 604/890.1 |
| 4,983,395 | 1/1991 | Chang et al. | 424/448 |
| 5,069,909 | 12/1991 | Sharma et al. | 424/449 |
| 5,240,711 | 8/1993 | Hille et al. | 424/448 |
| 5,273,755 | 12/1993 | Venkatrama | 424/448 |

FOREIGN PATENT DOCUMENTS

| | | | |
|---|---|---|---|
| 0368409 | 5/1990 | European Pat. Off. | A61K 31/485 |
| 0432945 | 6/1991 | European Pat. Off. | A61L 15/44 |

OTHER PUBLICATIONS

Duragesic ™ (fentanyl transdermal system), *Physician's Desk Reference*, 47th Edition, 1993, pp. 1160–1164.

*Primary Examiner*—D. Gabrielle Phelan
*Attorney, Agent, or Firm*—Steinberg, Raskin & Davidson, P.C.

[57] ABSTRACT

A transdermal patch useful for evaluating the therapeutic effectiveness of a transdermally delivered medicinal agent is disclosed. The patch includes a substantially impermeable backing layer, a delivery layer containing a medicament and a substantially impermeable blocking layer. The delivery layer is arranged between the backing and blocking layers to prevent the release of the medicament contents from the delivery layer when the transdermal patch is affixed to the skin of a mammal. In alternative embodiments, non-transdermal placebo systems such as oral dosage forms which are coated with substantially impermeable layers to create virtually identical placebos of active oral delivery systems such as tablets, capsules and osmotic tablets are disclosed. Methods of comparing the therapeutic effectiveness of active dosage forms, i.e. transdermal units containing a medicament to placebo or to comparable active agents in either similar or different delivery systems are also disclosed.

9 Claims, 3 Drawing Sheets

TRANSDERMAL PATCH FOR COMPARATIVE EVALUATIONS

This application claims the benefit of U.S. Provisional application Ser. No. 60/008,391, filed Dec. 8, 1995, now abandoned.

BACKGROUND OF THE INVENTION

The present invention relates in general to the preparation of placebo formulations for use in clinical evaluations of pharmaceutical products. In particular embodiments, the invention relates to a transdermal placebo patch useful in clinical evaluations which facilitates comparative therapy evaluations of a transdermal unit dosage form and a non-medicated control.

A standard in medical research is a double blind study or trial. A double blind study requires that both the doctor and the patient not know which drug they are being given. Double blind trials are of two types: placebo controlled and active controlled. When one is testing an agent for a condition in which there is no proven effective treatment, the comparison agent is a placebo dosage form that is made to look identical to the active test agent. When one wants to explore the advantages and differences between two active agents, it is necessary to make the two agents look identical to the patient and the doctor. For example, those skilled in the art often place tablets and capsules into larger, opaque capsules in these types of experiments. However, what is one to do in comparing a tablet to a clear patch that is about one inch by three inches in size, with clear trademarks written on the patch?

Double blind comparative evaluations for parenteral medications are easiest to carry out. The identity of the medication undergoing evaluation and the control or placebo can be easily concealed from the patient since both are typically administered as a clear solution in an unmarked syringe. Oral medications are also relatively easy to clinically evaluate for effectiveness. Manufacturers can often easily prepare dosage forms which are strikingly similar to a dosage form which contains the medicinal agent under consideration. Thus, in the case of parenteral and oral dosage forms, drug manufacturers can conduct clinical evaluations and double blind studies with relative ease and with a high level of confidence that patient bias has not skewed the results.

In recent years, some pharmaceutical manufacturers have been promoting the use of the transdermal route of administration as an alternative to the traditional routes of administration. Clinical evaluations of transdermally-delivered medications, especially as part of double blind studies, have been difficult to carry out. For example, if a manufacturer wishes to compare the effectiveness of its transdermally-delivered agent against a currently marketed transdermal product, the test subjects are immediately aware of the differences in appearance between the two products. The differences also tend to be magnified since the patch is affixed to the patient for extended periods of time and the visual and tactile differences are reinforced. Transdermal patches are significantly more difficult to disguise or copy, even if one overlooks the issues associated with adulterating and/or misbranding currently available transdermal patches. Briefly stated, it is often very difficult to mimic the "look and feel" of commercially available transdermal patches so as to avoid bias in clinical evaluations.

The classical solution, the double-blind, double-dummy active controlled trial is impractical because those skilled in the art believed it necessary to manufacture a drug-free facsimile of a commercially available transdermal patch. This approach involves making a placebo for each of the two active agents that are being compared. For example, such a controlled trial might involve each patient taking one active and one placebo at the times of treatment. About half the patients (randomly selected) are administered the test agent (e.g., a commercially available tablet containing a drug) and the control agent (placebo) patch, and the balance are administered the test placebo (a placebo of commercially available tablet) and a transdermal patch containing a drug. However, such a clinical trial is extremely difficult to conduct in cases where the active transdermal patch (e.g., commercially available) is manufactured by a third party. The difficulty lies in duplicating the third-party patch in a placebo form. This is especially problematic where the active patch is unusual in design. Also, such an active patch would typically have the name era third party competitor's product on the packaging and the patch, which identities are the property of the third-party competitor. Thus, manufacture of a placebo version era transdermal patch which includes the identity of a third party and its trademark may pose additional problems legally. Unfortunately, obtaining inactive, placebo versions of a transdermal product to be comparatively studied from the manufacturer itself is in many cases out of the question.

Of course, the same issues are raised when the two actives to be compared are both in the form of transdermal patches, and one of these transdermal patches manufactured and bears the identities belonging to a third party.

Over the years, medical practitioners have sought to reduce the number of times a day that a medication is administered to patients. To this end, significant effort has been directed to developing transdermal delivery systems which deliver a needed medication at a uniform rate over an extended period of time. The practicality of administering a given drug percutaneously, however, depends upon several factors. For example, the concentration of drug in the blood that is required to effect the desired therapy, how permeable the skin is to the desired drug, the amount of surface area that can practically be used for administration as well as other factors, all play a role in determining whether the transdermal mute is appropriate for a particular drug. For example, certain drugs such as nicotine, nitroglycerine or estrogens have been successfully developed as relatively small transdermal patches which have high levels of patient acceptance.

There are many patents which describe devices for administering drugs through the skin. These references often describe laminated composites that include a delivery or reservoir layer containing a drug, a pressure sensitive adhesive layer for attaching the composite to the skin and a backing layer that forms the outer layer of the laminate. Other systems incorporate the active agent into a matrix and/or an adhesive formulation which is deposited on an inert backing layer. Depending on the drug and formulation required, the drug can be dispersed in a matrix or a walled delivery portion of the patch. In either case, a fixed amount of the drug is permitted to exit the patch over a given time period.

Once the flux of delivery is established (usually measured in $mg/cm^2/hour$) and the physical dimensions are established, the rate of drug delivery across the dermal layers can be theoretically calculated and empirically measured and the type of transdermal device has been selected, manufacturers must eventually submit their product to clinical evaluations. These evaluations are often more difficult than those used to evaluate parenteral or oral medications.

In view of the increasing acceptance by the public of transdermally delivered medications, there is a need to develop more effective clinical evaluation techniques for carrying out double blind clinical evaluations of transdermal medicines. The present invention addresses this need.

SUMMARY OF THE INVENTION

It is an object of the invention to provide medical devices which function as control or placebo transdermal unit dosage forms for clinical evaluations.

It is also an object of the present invention to provide an improved method of clinically evaluating the therapeutic effectiveness of transdermally-delivered medications.

Another object of the present invention is to provide a method of conducting double blind evaluations of transdermal unit dosage forms.

A further object of the present invention is to provide a method of determining the pharmacokinetic and pharmacodynamic parameters obtained from a transdermal patch delivering a medicament.

These and other objects are achieved by the present invention which, in one embodiment, includes a transdermal patch containing:

a) a substantially impermeable backing layer;

b) a delivery layer or layers containing an active ingredient;

c) an adhesive layer to both affix the delivery device to the skin or mucosa; and d) means for blocking delivery of the active agent from the transdermal patch, e.g., a substantially impermeable blocking layer.

The delivery layer is affixed between the substantially impermeable backing layer and the substantially impermeable blocking layer. The blocking layer prevents the release of delivery layer contents when the transdermal patch is in contact with the skin of a patient, thus providing a matching placebo of a commercially available active transdermal patch.

In another aspect of the invention, there is provided a method of clinically testing a transdermal patch containing a medicament and comparing the pharmacokinetic and pharmacodynamic parameters provided by the transdermal patch to a placebo of a commercially available transdermal patch containing a comparable medicament, comprising:

a) providing a first transdermal patch containing a medicament in a delivery layer;

b) providing a second transdermal patch as a placebo of a commercially-available transdermal patch containing a comparable medicament in a depot that cannot deliver the comparable medicament;

c) conducting a double blind clinical test on test subjects wherein each subject receives either the first or second transdermal patch; and d) comparing the pharmacokinetic and pharmacodynamic data obtained from the test subjects who received the first transdermal patch to the pharmacokinetic and pharmacodynamic data obtained from the test subjects who received the second transdermal patch.

In this aspect of the invention, the second transdermal patch is designed to have an appearance which is substantially identical to that of the first patch and includes a substantially impermeable blocking layer which prevents the release of the comparable medicament from the patch when affixed to the skin of a subject. The blocking layer can be a thin and transparent impermeable membrane which is coated with an inert pharmaceutically-acceptable adhesive which matches that used in the commercially-available form so as to mimic the appearance of the patch.

A still further embodiment of the invention includes a method of clinically testing a transdermal patch containing a medicament and comparing the pharmacokinetic and pharmacodynamic parameters provided by the transdermal patch to a placebo of a commercially-available transdermal patch containing a comparable medicament. The method includes:

a) providing a first transdermal patch containing a medicament in a delivery layer;

b) manipulating a commercially available transdermal patch containing a delivery layer having a comparable medicament therein to block the release of the comparable medicament while substantially maintaining the of appearance the commercially available transdermal patch;

c) administering each of the first transdermal patch and the manipulated commercially available transdermal patch to test subjects according to a double blind protocol; and d) comparing the pharmacokinetic and pharmacodynamic data obtained from the first transdermal patch to the pharmacokinetic and pharmacodynamic data obtained from the manipulated commercially-available transdermal patch.

In this aspect of the invention, the commercially-available transdermal patch is manipulated to block the release of the comparable medicament from delivery by applying a cross linking agent or by causing the elements of the delivery layer to cross-link and bind the active agent into a non-releasable form. The cross-linking agent selectively binds to the comparable medicament and prevents the release of the comparable medicament from the delivery portion of the system.

As a result of the present invention, there are provided medical devices which allow pharmaceutical manufacturers to better clinically evaluate their transdermal formulations. Products of the present invention serve as placebos which substantially match the look and feel of commercially-available transdermal unit dosage forms containing active ingredients. Furthermore, clinical evaluations such as double blind studies where subjective data is generated, i.e. analgesia, pain relief, etc. can be carried out without the inherent bias caused by patients being given transdermal products having discernable differences in look and feel.

For a better understanding of the present invention, together with other and further objects, reference is made to the following description, taken together with the accompanying drawings, and its scope will be pointed out in the appended claims.

DETAILED DESCRIPTION OF THE INVENTION

Figure 1:
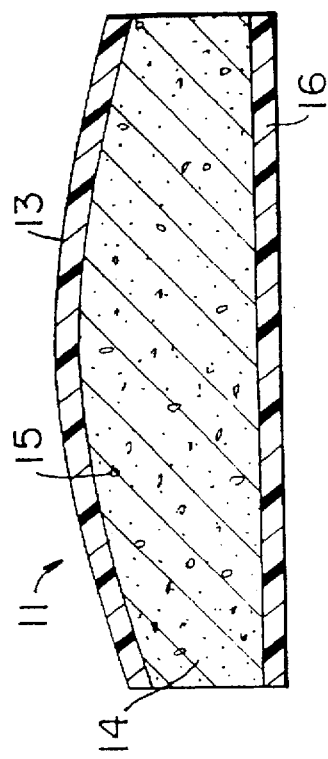
FIG. 1 is a sectional schematic view of a transdermal patch prepared in accordance with the present invention.

Referring now to the Figures, certain preferred aspects of the present invention are illustrated. It is to be understood that the transdermal placebo patches described herein are not limited to the types of transdermal systems shown in the figures and that transdermal systems such as monolithic or reservoir systems can also be manipulated to block release of the medicaments contained therein using the techniques described and claimed herein. In FIG. 1, there is provided a placebo self-adhering transdermal patch 11 that is designed to be placed on the skin of a patient. The patch 11 is a laminate that consists of three layers. A top backing layer 13 which is substantially impermeable, a delivery layer 14 containing an active ingredient 15 and a substantially impermeable blocking layer 16.

The backing layer 13 defines the top of the patch. It is made from one or a combination of materials that are substantially impermeable to the contents of the delivery 14. Thus, the backing layer serves as a protective cover for the delivery 14, keeps the components of the delivery from escaping from the patch along the surfaces which it shares a common border and fulfills a structural support function. Examples of materials that may be used to make the backing layer include high and low density polyethylene, polypropylenes, polyvinyl chlorides, polyethylene terephthalates and mixtures thereof.

Figure 2A:
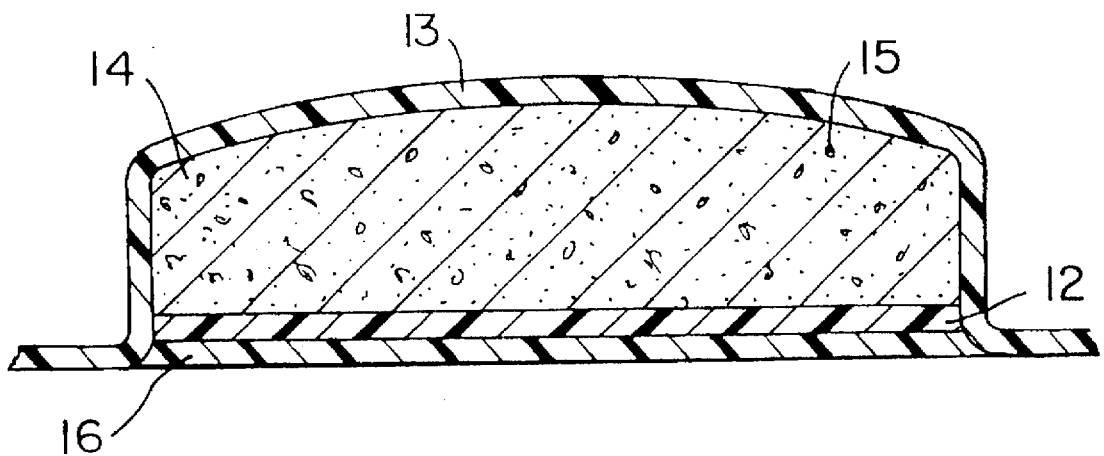
FIG. 2a is a sectional schematic view of a transdermal patch prepared in accordance with the present invention illustrating the blocking layer affixed to the diffusion membrane layer of a transdermal patch.
Figure 2B:
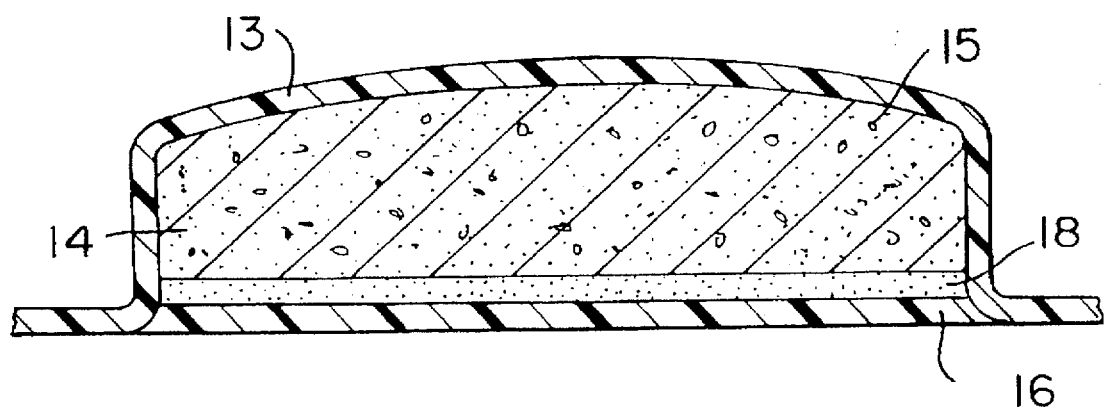
FIG. 2b is a sectional schematic view of a transdermal patch prepared in accordance with the present invention illustrating the blocking layer affixed to the pressure sensitive adhesive layer of a transdermal patch.

In certain embodiments of the invention, the delivery layer 14 includes a fluid contained within a shell-like matrix. The outer edge of the backing layer will overlay the edge of the delivery layer and be sealed by adhesion or fusion. Alternatively, the delivery layer can be fused to a diffusion membrane layer 12 as shown in FIG. 2a or pressure sensitive adhesive layer 18 as shown in FIG. 2b if the delivery layer 14 is not designed to include a pressure sensitive adhesive. In such structures, the delivery layer is contained wholly between the backing layer and the diffusion membrane layer 12 or pressure sensitive adhesive layer 18 and does not have any exposed surfaces. The backing layer 13 is designed to be sealable with the other components of the transdermal unit and include sealing means such as an additional layer of adhesive in which the delivery layer 14 can be attached to the backing layer 13. In each case, however, the substantially impermeable blocking layer 16 is designed to be directly affixed to the layer designed for the commercially available transdermal patch to be in contact with the skin. It is also to be understood that the blocking layer 16 is permanently affixed to the transdermal patch and completely seals off the release of any active ingredient 15.

Figure 3:
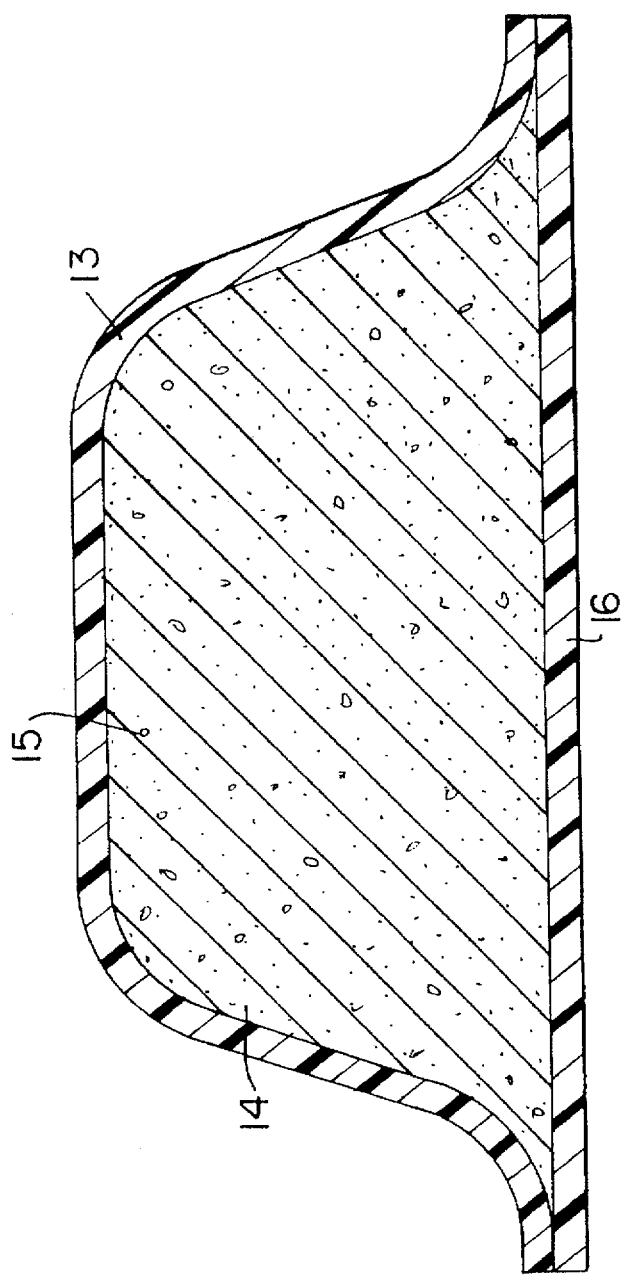
FIG. 3 is a sectional schematic view of a transdermal patch prepared in accordance with the present invention illustrating the blocking layer affixed to a delivery layer of a transdermal patch containing a pressure sensitive adhesive.

Referring now to FIG. 3, there is shown an alternative embodiment of the present invention. In particular, this aspect of the invention provides a placebo for a transdermal unit dosage form designed so that the delivery layer 14 also includes a pressure sensitive adhesive as part of the delivery matrix. Such delivery layers in some commercially available transdermal dosage units are designed to facilitate direct transfer of a medicament from the patch to the patient. In this aspect, the substantially impermeable blocking layer 16 is directly affixed to the delivery layer 14 and enough of the backing layer 13 so as to achieve the blockage of active ingredient release.

It will be understood that the placebo patches of the present invention will require that the barrier layer affixed to any pressure sensitive adhesive containing or transporting a deliverable drug be interposed between the active adhesive surface and the patient and also serve to affix the placebo when used in the trial. In this regard, the barrier layer can be prepared to include one or more of the pressure sensitive adhesives so that the blocking layer can adhere to the unit one side to block the release of the drug contained in the delivery layer and, on the other side, allow the transdermal placebo patch to be affixed to the skin. In certain aspects of the invention, the blocking layer will require a pressure sensitive adhesive on at least one of its two sides. Such materials can be selected from pharmaceutically acceptable adhesive materials such as isobutylenes, silicones, or acrylate adhesives. Representative adhesives include polyisobutylene, silicone adhesives such as silastic, Dow Corning X7-2920 silicone adhesive or Dow Corning 2675 silicone adhesive with or without added silicone-oil tackifiers and solvent-based or water-based acrylate materials. Acrylate copolymers are available commercially such as, for example, from Monsanto Chemical Co. under the trademark Gelva for vinyl acetate-acrylate copolymer resin solutions and from Morton Thiokol, Inc. under the trademark Morstik for acrylate copolymers can also be used. In preferred aspects of the invention, the same or similar materials as that used for the backing layer of the commercially-available transdermal system is used since, by design, the backing layer is impermeable to the active agent included therewith.

For ease of manufacture, in preferred aspects of the invention, the placebo transdermal patches are prepared by modifying commercially-available transdermal unit dosage forms. Such units, typically include the delivery layer 14 is immediately below the backing layer 13. The delivery layer contains a predetermined amount of a drug 15 and optional ingredients such as an enhancer to assist entry of the drug through the skin barrier. The amount of drug and enhancer in the delivery layer will depend upon the medicament included in the commercially-available transdermal patch, the rate at which the enhancer is administered to the skin from the delivery layer and the rate of release of the medicament from the delivery layer, among other variables. The delivery layer 14 may also be include diluent, stabilizers, vehicles, gelling agents, preservatives and the like depending upon the commercially available transdermal patch selected. The products of the present invention, however, are designed to block the release of substantially all such substances via the attachment of the substantially impermeable blocking layer 16. The substantially impermeable blocking layer can be a thin and transparent membrane which is either singly or doubly coated with an inert pharmaceutically-acceptable adhesive which is the same as that found on the commercially-available transdermal patch or one which is substantially similar thereto so as to not detract from the physical and/or visual characteristics of the manipulated patch.

In one aspect of the invention, the transdermal patches of the present invention are prepared by removing the commercially available transdermal patches from any protective packaging and removing the peelable protective layer, if utilized by the manufacturer. The substantially impermeable blocking layer 16 is then applied to the transdermal patch 11 to cover the layer originally designed to come in contact with the skin with a suitable adhesive. The transdermal placebo patch can then be affixed with a peelable protective layer, not shown, and packaged for later use by a clinician in a clinical evaluation if desired. Prior to use on a patient, the peelable protective layer is removed from the blocking layer 16 and discarded. This peelable layer is made from materials which are inert with respect to the materials contained in the transdermal unit dosage form and can be made from the same materials as those described above concerning the backing layer 13, a non-porous plastic or polyester or even a metal foil.

The substantially impermeable blocking layer 16 is designed to be compatible with extended periods of contact with the skin. Furthermore, since the layer acts as a barrier, it is understood that it is made from one or a combination of materials that are substantially impermeable to the contents of the delivery layer 14 and thus insure a placebo effect is obtained when the unit is affixed to the skin. Suitable materials include high and low density polyethylene, polypropylenes, polyvinyl chlorides, polyethylene terephthalates and mixtures thereof. Alternatively, the barrier can be prepared as a laminate containing a non-porous blocking layer and an upper adhesive layer for affixing the barrier to the commercially available transdermal unit dosage form and a lower adhesive layer for attaching the transdermal unit 11 to the skin of the patient. It is also contemplated that if the commercially available transdermal unit is designed to be affixed to the skin via a pressure sensitive or other adhesive means found only on the backing layer, then the lower adhesive laminae is to be considered optional. For example, depending upon the type of transdermal placebo prepared, one or more of the individual components, i.e. the backing layer, delivery layer, adhesive membrane layer, barrier layer, etc. will be coated with a contact adhesive so as to allow the transdermal placebo patch to be affixed to an area of the skin. The composition and thickness of the barrier layer is such that it is essentially integrated with the commercially available transdermal unit dosage form which is modified and does not constitute a significant distraction to the patient by way of adding physical bulk or weight to the patch. Furthermore, the barrier layer is also preferably designed to contact the skin in a manner which essentially duplicates the physical sensation of the commercially available unit's contact skin layer. In many cases, the same adhesive system may be satisfactorily employed so that the altered placebo produced will adhere and release from the skin in the same way as the active patch.

In further aspects of the invention, substantially impermeable blocking layers are not included to achieve the placebo effect. Rather, the release of the active ingredient contained in a commercially-available transdermal system is blocked by applying a cross-linking agent to the pressure-sensitive adhesive layer which transforms the otherwise drug-permeable adhesive layer to a non-permeable barrier. The cross-linking agent can be applied to the pressure sensitive adhesive layer or diffusion membrane layers if found on the commercially-available transdermal product. Alternatively, cross-linking may be achieved by exposing the active patch to ionizing radiation which can also cross-link the polymeric pressure sensitive agents used in some commercially-available transdermal formulations.

Still further aspects of the invention include manipulating commercially-available transdermal systems containing a medicament to block the release of the medicament by applying a selectively-permeable or impermeable membrane to the delivery portion of the system, pressure sensitive adhesive layer or diffusion membrane layers. Such membranes can selectively block the release of the medicament, for example, by binding the active ingredient to the blocking membrane using affinity charge technology similar to that used in ion-exchange chromatography. Alternatively, hydrophilic/hydrophobic interaction techniques can be used if the medicament being blocked is capable of being repelled from release by such non-chemical interactions. A still further alternative blocking layer includes a selectively permeable membrane which contains an average pore size which blocks the release of the medicament. Combinations of the foregoing blocking layers are also contemplated.

In another aspect of the invention, there is provided a method of clinically testing a transdermal patch containing a medicament in order to compare its pharmacokinetic and pharmacodynamic parameters to a control or a placebo of a commercially available transdermal patch containing a comparable medicament.

Pharmacokinetic is a discipline that deals with the rates of movement of a drug or its metabolites into the body, among its many compartments, and out of the body (i.e., the absorption, distribution, biotransformation and excretion of drugs).

Pharmacodynamics deals with the biochemical and physiological effects of drugs and their mechanisms of action. Operationally, pharmacokinetic may be defined as what the body does to the drugs and pharmacodynamics may be defined as what the drug does to the body. Extensive clinical studies are required before regulatory approval of even a close derivative of a well-known drug.

Accordingly, the method of clinically testing includes:

a) providing a first transdermal patch containing a medicament in a delivery layer;

b) providing a second transdermal patch as a placebo of a commercially available transdermal patch containing a comparable medicament, the second patch having an appearance which is substantially identical to the first patch and a substantially impermeable blocking layer which prevents the release of the comparable medicament in the second patch;

c) administering the first and the second transdermal patches to test subjects according to a double blind protocol; and d) comparing the pharmacokinetic and pharmacodynamic data obtained from the test subjects who received the first transdermal patch to that data obtained from the test subjects who received the second transdermal patch.

For purposes of the present invention, the term "comparable medicament" shall be understood to mean a medicament which has a therapeutic effect which is the same or substantially the same as the medicament undergoing the comparative evaluation. For example, certain members of the opioid family are considered to be therapeutically equivalent in terms of relieving a particular level, i.e. mild to moderate, of pain. The term shall also be understood to include generic equivalents.

Also for purposes of the present invention, the term "clinically testing" shall be understood as including controlled clinical trials which include sufficient and adequate sampling to allow projections to be made for larger populations. The term shall also be understood to include random assignment of test subjects to each of the testing groups.

In accordance with this aspect of the invention, the transdermal patches of the present invention, such as those based on a commercially-available transdermal patch engineered to contain a blocking layer, as described above, are preferably used as the second transdermal patch in the method described herein.

The methods of this aspect of the invention preferably include a double blind clinical evaluation. The placebo transdermal patches of the present invention have substantial identity of appearance with the transdermal patch undergoing evaluation and thus substantially eliminate any bias generated by differences in appearance or tactile sensations. Since the barrier layer need be a few microns in thickness, the patient is unaware whether he is receiving the medicament or not during the clinical evaluation. For example, during the clinical evaluation, identical looking transdermal patches are applied to a relatively non-hairy area of the skin that is substantially free of wrinkles, creases or folds. Various locations on the torso, such as the flank or shoulder provides suitable areas for affixing the transdermal patch.

In a still further embodiment of the invention, the placebo transdermal systems of the present invention are included in controlled clinical trials used to compare the therapeutic effect of a transdermally-delivered medicament with that obtained using a different dosage system such as an oral tablet or capsule. Since the transdermal type of delivery is so different from the oral route, the method includes conducting a double-blind controlled trial in which double-dummy (placebo) and active dosage forms are used. In this embodiment, a protocol such as one which is well-known to those of ordinary skill in the art can be used so that each of the active agents is paired with its matching placebo. Clinical supplies are packaged for each subject in the investigation to assure that each subject will receive both type of delivery systems, but for any subject at a point in time, only one of the two systems is active and the other is a placebo. This approach is easily facilitated by the present invention that provides for the production of a placebo by taking the active agent and blocking the functioning of the delivery system in a way that is difficult or impossible for the patient to detect.

The blocking of the release of medicament in transdermal systems can also be applied to non-transdermal systems such as oral delivery systems. For example, a tablet or capsule containing a medicament and a delivery system can be inactivated by overcoating the oral dosage form with an impermeable polymeric layer which is insoluble in the gastrointestinal system environment. If necessary and desirable, the active tablet, capsule, or osmotic pump tablet can also be overcoated with an inert and highly soluble layer such as CMC to provide a visual and physical appearance which approximates that of the active delivery system. The two dosage forms would appear the same, yet the placebo would be created from the active through a deliberate process of blocking the performance of the delivery system.

EXAMPLES

The following examples serve to provide further appreciation of the invention but are not meant in any way to restrict to the effective scope of the invention.

Example 1

Figure 4A:
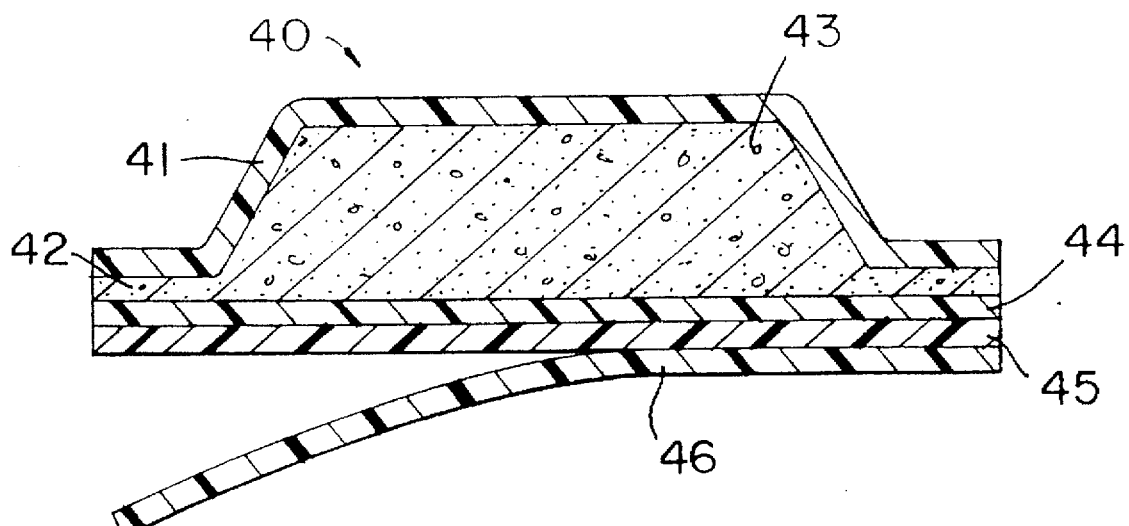
FIG. 4a is a sectional schematic view of a commercially available transdermal patch containing fentanyl.

In this example, a placebo of the commercially available transdermal analgesic DURAGESIC™ (fentanyl transdermal systems) patches designed to release 25 µg/hr/10 cm² dose is undertaken. A schematic representation of the transdermal patches obtained from the manufacturer is shown in FIG. 4a. The patch 40 includes a backing layer 41 of a polyester film, a drug delivery 42 containing fentanyl 43 and other ingredients such as alcohol U.S.P. gelled with hydroxyethylcellulose, a release membrane 44 composed of an ethylene-vinyl acetate copolymer which controls the rate of fentanyl delivery to the skin surface, and a fentanyl-containing silicone adhesive layer 45. Also shown, partly pealed away is a protective layer 46 which covers the adhesive layer 44 until the unit is needed for use.

Figure 4B:
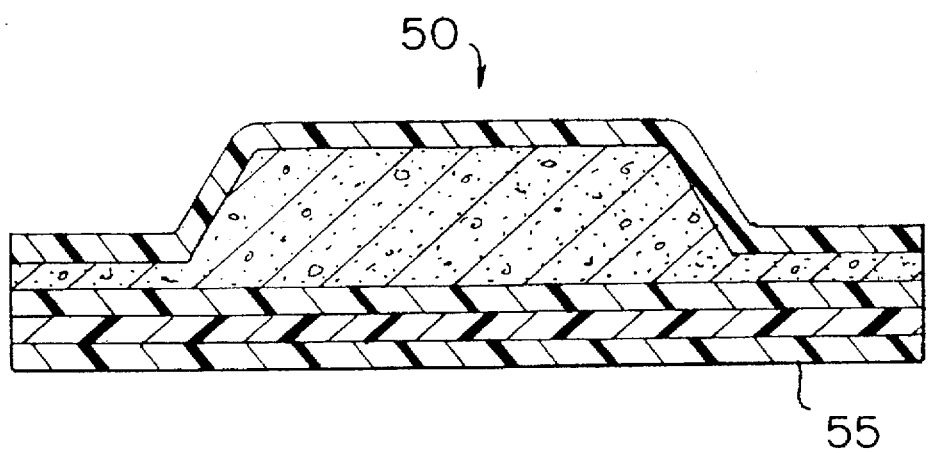
FIG. 4b is a sectional schematic view of a commercially available transdermal patch containing fentanyl containing a blocking layer in accordance with the present invention.

In order to prepare the fentanyl transdermal placebo 50, as shown in FIG. 4b, the protective liner (not shown) is removed and a substantially impermeable blocking layer 55 is applied to the patch using an adhesive polymer solution sold by Dow Corning as DC-355. On the opposite side of the substantially impermeable blocking layer, the same silicone adhesive material found on the commercially available patch to facilitate attachment of the unit to the skin is applied. It is to be noted that the transdermal placebo patch illustrated in FIG. 4b is not shown to scale but in actual appearance, the placebo unit is substantially similar to that of the DURAGESIC™. It is to be noted that the blocking layer 55 effectively eliminates any release of fentanyl and has a width of less than about 50–75 microns which is virtually undetectable to a patient. Finally, the placebo patch 50 can have a protective layer (not shown) affixed to the blocking layer 55 so as to preserve the adhesiveness of the outermost layer until the unit is needed.

Example 2

The procedure of Example 1 is repeated except that placebo transdermal patches for Transdermal Nitro™ 0.1 mg per hour (2.5 mg per 24 hours) patches (Summit Pharmaceuticals) are prepared. The placebo patch is found to have a substantially identical appearance as the commercially available patch. The difference in thickness between the two patches is virtually undetectable because the blocking layer is only approximately 50 microns.

Example 3

In this example, fentanyl-containing transdermal patches designed to contain the same amount of fentanyl as that found in the commercially available DURAGESIC patches used in Example 1, i.e. releasing 25 µg/hr/10 cm², are prepared. Before the regulatory approval of the generic equivalent product is sought, a clinical determination of the pharmacokinetic and pharmacodynamic parameters of the new product is undertaken. Ten adult males are randomly assigned in a double blind study to receive either the new fentanyl-containing transdermal patches or placebo DURAGESIC™ patches prepared in the manner described in Example 1. On day 1, each patient is given either the fentanyl-containing transdermal patch (applied to the skin) or the DURAGESIC™ placebo transdermal patch. On day 4, the respective patches are removed and replaced with a second patch of the same type, and this step is repeated on day 7, day 10 and day 13. On day 16, the patch applied on day 13 is removed and each member of the group is followed through day 19.

Pharmacokinetics

The fentanyl-containing transdermal patch is found to release the fentanyl from the delivery layer at a nearly constant rate per unit time. The concentration gradient existing between the saturated solution of the drug and the delivery layer and the lower concentration in the skin facilitates release of fentanyl through the skin. During the course of the study, it is determined that serum fentanyl concentrations increase gradually and generally level off between 12 and 24 hours after administration and remain relatively constant with a limited amount of fluctuation for the remainder of the 72 hour (4 day administration periods). Peak serum levels of the fentanyl are generally obtained between 24 and 72 hours after a single application of a transdermal patch. Furthermore, serum fentanyl concentrations achieved are determined to be proportional to the fentanyl delivery rate after sequential 72 hour applications, the patients are found to reach a steady state serum concentration. After the transdermal system are removed, the serum fentanyl concentrations decline gradually, falling about 50% approximately 17 hours. Continued absorption of fentanyl from the skin accounts for a slower disappearance of the drug from the serum than that seen, for example, in IV infusions where the apparent half-life ranges from about 3 to about 12 hours. The subjects receiving the placebo transdermal patch displayed no fentanyl absorption.

Additional pharmacokinetic data was also obtained: the average volume of distribution of fentanyl for the patients is determined to be six liters per kilogram. The average clearance in patients is determined to be 46 liters per hour. It is also determined that the skin does not appear to metabolize fentanyl delivered transdermally. Human keratinocyte cell assay and clinical studies determine that about 92% of the dose delivered from the transdermal system is accounted for as unchanged fentanyl in systemic circulation.

Pharmacodynamics

Analgesia

The minimum effective analgesic serum concentration of the fentanyl is determined to be from about 0.2 to about 1.2 mg per ml.

Example 4

In vitro tests were carried out to determine the flux of the fentanyl from the patches compared in Example 3 and compared to that obtained from the placebo-rendered DURAGESIC™ patches prepared as a result of Example 1. The in vitro fentanyl skin flux from the system without the barrier layer is determined is determined to be about 25 g/hr/10 cm². On the other hand, the placebo patches prepared in accordance with Example 1 are determined to have essentially no release of fentanyl from the modified DURAGESIC patches.

Example 5

Clinical Trials

The fentanyl transdermal patches prepared in Example 3 are compared against placebo DURAGESIC patches prepared as set forth in Example 1 in patients with acute and chronic pain (postoperative and cancer pain models) using a double blind study where randomly assigned subjects (group of 10 patients) received one transdermal patch per day for 7 days. The analgesia of the fentanyl-containing patches is demonstrated at the end of the study to effectively manage acute and chronic pain.

Example 6

The procedure of Example 1 is repeated except that the placebo transdermal patches were prepared by affixing a selectively permeable membrane across the silicone adhesive layer. The placebo patch is found to have a substantially identical appearance as the commercially available patch. The difference in thickness between the two patches is virtually undetectable because the blocking layer is only approximately 50 microns. In vitro testing indicates that no fentanyl is released from the placebo-rendered patch.

What is claimed is:

1. A transdermal placebo patch comprising:
   a) a substantially impermeable backing layer;
   b) a delivery layer containing an active ingredient; and
   c) a crosslinking agent,
   wherein said crosslinking agent selectively binds to said active ingredient preventing the release of contents from said delivery layer when said transdermal placebo patch is affixed to the skin of a mammal.

2. The transdermal placebo patch of claim 1, further comprising a pressure sensitive adhesive for affixing said transdermal placebo patch to the skin of a mammal.

3. The transdermal placebo patch of claim 2, wherein said pressure sensitive adhesive comprises a polymer selected from the group consisting of acrylates, methacrylates and mixtures thereof.

4. A method of clinically testing a transdermal patch containing a medicament and comparing the pharmacokinetic and pharmacodynamic parameters provided by said transdermal patch to a placebo of a commercially available transdermal patch containing a comparable medicament, comprising:
   a) providing a first transdermal patch containing a medicament in a delivery layer;
   b) providing a second transdermal patch as a placebo of a commercially available transdermal patch containing a comparable medicament and having:
      i) an appearance which is substantially identical to said first patch and
      ii) a substantially impermeable blocking layer which prevents the release of said comparable medicament in said second patch;
   c) administering each of said first and said second transdermal patches to a test subject according to a double blind protocol; and
   d) comparing the pharmacokinetic and pharmacodynamic data obtained from said first transdermal patch to that obtained from said second transdermal patch.

5. The method of claim 4, wherein said comparable medicament is a generic equivalent the medicament in said first transdermal patch.

6. The method of claim 5, wherein said substantially impermeable blocking layer further comprises a pressure sensitive adhesive for affixing said second transdermal patch to the skin of a mammal.

7. A method of clinically testing a transdermal patch containing a medicament and comparing the pharmacokinetic and pharmacodynamic parameters provided by said transdermal patch to a placebo of a commercially available transdermal patch containing a comparable medicament, comprising:
   a) providing a first transdermal patch containing a medicament in a delivery layer;
   b) manipulating a commercially available transdermal patch containing a reservoir having a comparable medicament therein so as to block the release of said comparable medicament while substantially maintaining the appearance of said commercially available transdermal patch;
   c) administering each of said first transdermal patch and said manipulated commercially available transdermal patch to test subjects according to a double blind protocol; and
   d) comparing the pharmacokinetic and pharmacodynamic data obtained from said first transdermal patch to the pharmacokinetic and pharmacodynamic data obtained from said manipulated commercially available transdermal patch.

8. A method of clinically testing a transdermal patch containing a medicament and comparing the pharmacokinetic and pharmacodynamic parameters provided by said transdermal patch to a placebo of a commercially available transdermal patch containing a comparable medicament, comprising:

a) providing a first transdermal patch containing a medicament in a delivery layer;

b) manipulating a commercially available transdermal patch containing a reservoir having a comparable medicament therein so as to block the release of said comparable medicament while substantially maintaining the appearance of said commercially available transdermal patch, wherein said blocking of the release of said comparable medicament is achieved by applying a cross linking agent to said reservoir which selectively binds to said comparable medicament and prevents the release of said comparable medicament;

c) administering each of said first transdermal patch and said manipulated commercially available transdermal patch to test subjects according to a double blind protocol: and d) comparing the pharmacokinetic and pharmacodynamic data obtained from said first transdermal patch to the pharmacokinetic and pharmacodynamic data obtained from said manipulated commercially available transdermal patch.

9. A method of clinically testing a transdermal patch containing a medicament and comparing the pharmacokinetic and pharmacodynamic parameters provided by said transdermal patch to a placebo of a commercially available transdermal patch containing a comparable medicament comprising:

a) providing a first transdermal patch containing a medicament in a delivery layer;

b) manipulating a commercially available transdermal patch containing a reservoir having a comparable medicament therein so as to block the release of said comparable medicament while substantially maintaining the appearance of said commercially available transdermal patch, wherein said blocking of the release of said comparable medicament is achieved by applying a selectively permeable membrane to said reservoir which selectively blocks the release of said comparable medicament;

c) administering each of said first transdermal patch and said manipulated commercially available transdermal patch to test subjects according to a double blind protocol; and d) comparing the pharmacokinetic and pharmacodynamic data obtained from said first transdermal patch to the pharmacokinetic and pharmacodynamic data obtained from said manipulated commercially available transdermal patch.

* * * * *